(12) United States Patent
Sevenster et al.

(10) Patent No.: US 12,292,893 B2
(45) Date of Patent: May 6, 2025

(54) AUTOMATED CONTEXTUAL DETERMINATION OF ICD CODE RELEVANCE FOR RANKING AND EFFICIENT CONSUMPTION

(71) Applicant: KONINKLIJKE PHILIPS N.V., Eindhoven (NL)

(72) Inventors: Merlijn Sevenster, Haarlem (NL); Paul Joseph Chang, Chicago, IL (US); Amir Mohammad Tahmasebi Maraghoosh, Arlington, MA (US)

(73) Assignees: Koninklijke Philips N.V., Eindhoven (NL); The University of Chicago, Chicago, IL (US)

( * ) Notice: Subject to any disclaimer, the term of this patent is extended or adjusted under 35 U.S.C. 154(b) by 189 days.

(21) Appl. No.: 16/087,694

(22) PCT Filed: Apr. 4, 2017

(86) PCT No.: PCT/EP2017/058006
§ 371 (c)(1),
(2) Date: Sep. 24, 2018

(87) PCT Pub. No.: WO2017/174591
PCT Pub. Date: Oct. 12, 2017

(65) Prior Publication Data
US 2019/0108175 A1 Apr. 11, 2019

Related U.S. Application Data

(60) Provisional application No. 62/319,923, filed on Apr. 8, 2016.

(51) Int. Cl.
G06F 16/2457 (2019.01)
G06F 16/2458 (2019.01)
(Continued)

(52) U.S. Cl.
CPC .... G06F 16/24578 (2019.01); G06F 16/2462 (2019.01); G06F 16/248 (2019.01);
(Continued)

(58) Field of Classification Search
CPC .... G06F 19/00; G06F 19/32; G06F 16/24578; G06F 16/2462; G06F 16/248;
(Continued)

(56) References Cited

U.S. PATENT DOCUMENTS

2002/0131625 A1* 9/2002 Vining .................. G16H 30/20
382/128
2003/0167189 A1* 9/2003 Lutgen .................. G16H 70/60
705/3

(Continued)

OTHER PUBLICATIONS

Goldstein, I. et al., "Three approaches to automatic assignment of ICD-9-CM codes to radiology reports". AMIA 2007 Symposium Proceedings p. 279-283.

*Primary Examiner* — Giovanna B Colan (57) ABSTRACT

A radiology workstation (24) includes at least one display component (30, 32); at least one user input device (28); and at least one microprocessor (26, 34) programmed to generate a contextual ranking of clinical codes for a context received via the at least one user input device (28) and to display information pertaining to the contextual ranking on the display component (30, 32) of the radiology workstation (24). The contextual ranking is computed by the microprocessor from (i) statistics of occurrences of the clinical codes in radiology reports contained in a radiology reports database (10) and satisfying the context and (ii) statistics of the clinical codes in problem lists contained in a problem lists database and satisfying the context.

17 Claims, 8 Drawing Sheets

(51) Int. Cl.
*G06F 16/248* (2019.01)
*G06F 40/205* (2020.01)
*G06F 40/289* (2020.01)
*G16H 15/00* (2018.01)
*G16H 50/70* (2018.01)
*G16H 10/20* (2018.01)
*G16H 50/20* (2018.01)

(52) U.S. Cl.
CPC .......... G06F 40/205 (2020.01); G06F 40/289 (2020.01); G16H 15/00 (2018.01); G16H 50/70 (2018.01); G16H 10/20 (2018.01); *G16H 50/20* (2018.01)

(58) Field of Classification Search
CPC ..... G06F 40/205; G06F 40/289; G16H 15/00; G16H 50/70; G16H 50/20; G16H 10/20
USPC .......................................................... 707/748
See application file for complete search history.

(56) References Cited

U.S. PATENT DOCUMENTS

| | | | | |
|---|---|---|---|---|
| 2007/0174079 A1* | 7/2007 | Kraus | .................... | G06Q 30/02 705/3 |
| 2007/0214013 A1* | 9/2007 | Silverman | .............. | G16H 50/30 600/300 |
| 2012/0035963 A1* | 2/2012 | Qian | ....................... | G16H 30/20 705/3 |
| 2012/0290319 A1* | 11/2012 | Saria | ...................... | G16H 10/60 705/3 |
| 2012/0296675 A1* | 11/2012 | Silverman | .............. | G16H 50/50 705/3 |
| 2014/0046694 A1* | 2/2014 | White | ..................... | G06Q 10/00 705/3 |
| 2014/0149407 A1* | 5/2014 | Qian | .................... | G06F 16/3331 707/737 |
| 2015/0149215 A1* | 5/2015 | Qian | ...................... | G16H 70/20 705/3 |
| 2015/0317337 A1* | 11/2015 | Edgar | .................... | G16H 50/70 707/751 |
| 2016/0004829 A1 | 1/2016 | Beqaj | | |
| 2016/0034664 A1* | 2/2016 | Santos | ................... | G16H 10/20 705/3 |
| 2016/0048660 A1* | 2/2016 | Lulias | .................... | G16H 10/60 705/3 |
| 2016/0232321 A1* | 8/2016 | Silverman | .............. | G16H 50/50 |
| 2016/0335403 A1* | 11/2016 | Mabotuwana | .......... | G16H 50/20 |
| 2017/0053074 A1* | 2/2017 | Enzmann | .............. | G06Q 10/103 |

* cited by examiner

FIG. 1

| Context | # of clinical history sections from which "I10" was extracted | # of clinical history sections examined | PROB (Code C is relevant) | # of problem lists that contain "I10" | # of problem lists examined | PROB ("I10" is in problem list) | Relevant |
|---|---|---|---|---|---|---|---|
| Abdomen | 134 | 33838 | 0.004 | 3074 | 7464 | 0.412 | 0.010 |
| Cardiac | 65 | 662 | 0.098 | 1344 | 2171 | 0.619 | 0.159 |
| Chest | 171 | 56671 | 0.003 | 3581 | 8470 | 0.423 | 0.007 |
| Neuro | 85 | 30930 | 0.003 | 1831 | 5946 | 0.308 | 0.009 |

Worked example for ICD10 code I10 (Hypertension)

FIG. 2

| Code | # of clinical history sections from which code was extracted | # of clinical history sections examined | PROB (Code C is relevant) | # of problem lists that contain code | # of problem lists examined | PROB (Code C is in problem list) | Relevant |
|---|---|---|---|---|---|---|---|
| C44.92 (Squamous cell carcinoma of skin, unspecified) | 0 | 33838 | 0 | 0 | 7464 | 0.123 | N/A |
| C44.9 (Other and unspecified malignant neoplasm of skin, unspecified) | 0 | 33838 | 0 | 0 | 7464 | 0.123 | N/A |
| C44 (Other and unspecified malignant neoplasm of skin) | 0 | 33838 | 0 | 0 | 7464 | 0.123 | N/A |
| C43-C44 (Malignant neoplasm, stated or presumed to be primary, of specified sites, except of lymphoid, haematopoietic and related tissue: Skin) | 10 | 33838 | 0.008 | 59 | 7464 | 0.123 | 0.012 |

The counts and estimated probabilities escalating ICD10 code C44.92 up the hierarchy in abdomen studies. No occurrences of C44.92, C44.9 and C44 are found in either Radiology report database or Problem list database. Finally, C44.92 receives the relevance score of the general code C43-C44, which is 0.012, reflecting low relevances

| Chronological | Abdomen | Cardiac | Chest | Neuro |
|---|---|---|---|---|

50

Merkel cell cancer - 5m 0d (0.24)
CRF (chronic renal failure) - 7m 11d (0.14)
Gynecomastia - 7m 11d (0.04)
S/P CABG x 2 - 6m 25d (0.02)
Hx of total hip arthroplasty - 7m 0d (0.02)
Former smoker - 7m 0d (0.02)
H/O pneumonectomy - 7m 0d (0.02)
Paroxysmal a-fib - 6m 27d (0.01)
Diabetes - 7m 11d (0.01)
Hypertension - 7m 11d (0.01)
CVA (cerebral infarction) - 6m 25d (0.01)
Obesity - 7m 11d (0)
CAD (coronary artery disease) - 7m 11d (0)
Perforation of bladder during operative procedure - 7m 0d (0)

Sample problem list ordered by relevance for abdomen study interpretation.
The value between brackets indicates the relevance score.

FIG. 5

| Chronological | Abdomen | Cardiac | Chest | Neuro |
|---|---|---|---|---|

CAD (coronary artery disease) - 7m 11d (0.29)
Hypertension - 7m 11d (0.16)
Diabetes - 7m 11d (0.12)
Obesity - 7m 11d (0.12)
Merkel cell cancer - 5m 0d (0)
S/P CABG x 2 - 6m 25d (0)
Former smoker - 7m 0d (0)
H/O pneumonectomy - 7m 0d (0)
Paroxysmal a-fib - 6m 27d (0)
CVA (cerebral infarction) - 6m 25d (0)
CRF (chronic renal failure) - 7m 11d (0)
Perforation of bladder during operative procedure - 7m 0d (0)
Hx of total hip arthroplasty - 7m 0d (0)
Gynecomastia - 7m 11d (0)

Sample problem list ordered by relevance for cardiac study interpretation.

FIG. 6

| Chronological | Abdomen | Cardiac | Chest | Neuro |

50

Merkel cell cancer - 5m 0d (0.12)
Paroxysmal a-fib - 6m 27d (0.1)
CRF (chronic renal failure) - 7m 11d (0.1)
CVA (cerebral infarction) - 6m 25d (0.06)
Hx of total hip arthroplasty - 7m 0d (0.04)
S/P CABG x 2 - 6m 25d (0.04)
H/O pneumonectomy - 7m 0d (0.04)
Former smoker - 7m 0d (0.04)
Gynecomastia - 7m 11d (0.01)
Diabetes - 7m 11d (0.01)
Hypertension - 7m 11d (0.01)
CAD (coronary artery disease) - 7m 11d (0)
Obesity - 7m 11d (0)
Perforation of bladder during operative procedure - 7m 0d (0)

Sample problem list ordered by relevance for chest study interpretation.

FIG. 7

| Chronological | Abdomen | Cardiac | Chest | Neuro |

CVA (cerebral infarction) - 6m 25d (0.43)
Merkel cell cancer - 5m 0d (0.14)
CRF (chronic renal failure) - 7m 11d (0.04)
Gynecomastia - 7m 11d (0.03)
Paroxysmal a-fib - 6m 27d (0.01)
Diabetes - 7m 11d (0.01)
Hypertension - 7m 11d (0.01)
Obesity - 7m 11d (0)
CAD (coronary artery disease) - 7m 11d (0)
Former smoker - 7m 0d (0)
Hx of total hip arthroplasty - 7m 0d (0)
H/O pneumonectomy - 7m 0d (0)
S/P CABG x 2 - 6m 25d (0)
Perforation of bladder during operative procedure - 7m 0d (0)

Sample problem list ordered by relevance for chest study interpretation.

FIG. 8

AUTOMATED CONTEXTUAL DETERMINATION OF ICD CODE RELEVANCE FOR RANKING AND EFFICIENT CONSUMPTION

CROSS-REFERENCE TO PRIOR APPLICATIONS

This application is the U.S. National Phase application under 35 U.S.C. § 371 of International Application No. PCT/EP2017/058006, filed on Apr. 4, 2017, which claims the benefit of U.S. Patent Application No. 62/319,923, filed on Apr. 8, 2016. These applications are hereby incorporated by reference herein.

FIELD

The following relates generally to the medical arts, the medical database arts, medical imaging arts, and related arts.

BACKGROUND

A feature of some Electronic Medical Record (EMR) systems (also known in the art by similar nomenclature such as Electronic Health Record, EHR systems) is providing for an EMR problem list (PL) that contains the patient's historical and current information in the form of International Classification of Diseases 10 (ICD-10) codes. This information may be valuable to a radiologist who is reading an imaging examination of the patient. The imaging examination may, for example, be a computed tomography (CT) imaging examination, a magnetic resonance (MR) imaging examination, a positron emission tomography (PET) imaging examination, a computed radiography (CR) imaging examination, or so forth. However, the PL for a patient can be lengthy and cumbersome to review as the majority of codes may be irrelevant for image interpretation. In practice, a radiologist may not consult the PL for the patient in performing a medical imaging examination reading.

The following provides new and improved devices and methods which overcome the foregoing problems and others.

SUMMARY

In accordance with one aspect, a radiology workstation includes at least one display component; at least one user input device; and at least one microprocessor programmed to generate a contextual ranking of clinical codes for a context received via the at least one user input device and to display information pertaining to the contextual ranking on the display component of the radiology workstation. The contextual ranking is computed by the microprocessor from (i) statistics of occurrences of the clinical codes in radiology reports contained in a radiology reports database and satisfying the context and (ii) statistics of the clinical codes in problem lists contained in a problem lists database and satisfying the context.

In accordance with another aspect, a non-transitory computer readable medium carrying software to control at least one processor to perform an image acquisition method is provided. The method includes: generating a contextual ranking of clinical codes for a context received via at least one user input device of a radiology workstation; and displaying information pertaining to the contextual ranking on a display component of the radiology workstation. The contextual ranking is generated from (i) statistics of occurrences of the clinical codes in radiology reports contained in a radiology reports database and satisfying the context and (ii) statistics of the clinical codes in problem lists contained in a problem lists database and satisfying the context.

In accordance with another aspect, a radiology workstation includes at least one display component and at least one user input device. At least one microprocessor is programmed to: generate a contextual ranking of clinical codes for a context received via the at least one user input device and to display information pertaining to the contextual ranking on the display component of the radiology workstation; and generate statistics of occurrences of the clinical codes in radiology reports by extracting a code C from radiology reports by performing natural language processing to identify phrases representing one or more clinical concepts corresponding to the clinical code C. The contextual ranking is computed by the microprocessor from (i) statistics of occurrences of the clinical codes in radiology reports contained in a radiology reports database and satisfying the context and (ii) statistics of the clinical codes in problem lists contained in a problem lists database and satisfying the context.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION

One possible approach for making the contents of the PL more useful for a radiologist is to rank ICD codes by relevance to medical imaging examination reading generally, or more particularly by relevance to the particular imaging examination (e.g. CT, MR, PET, . . . ) being performed. One approach is to provide (1) a rule based approach that determines ICD code-specific relevance and/or (2) a user interface device that lets the user provide feedback, which is used to create and calibrate rules. For instance, with regards to (1), it may assume that someone has entered the rule indicating that all codes in the "Neoplasm" category have relevance 0.8. Regarding option (2), one possible scenario is that one or more users have provided feedback in the workflow that all codes in the "Benign Neoplasm" category is less relevant than its containing category "Neoplasm". Both scenarios require manual input.

In illustrative approaches disclosed herein, relevance scores are derived for ICD codes without human interaction. The relevance scheme can be made contextual on various levels of granularity, also without human intervention. The disclosed approaches are based on the insight that mathematically, the problem of determining relevance can be defined as the conditional probability:

$$\text{PROB}(\text{Code } C \text{ is relevant} | \text{Code } C \text{ is in problem list } P) \quad (1)$$

By definition, this is equivalent to:

$$\text{PROB}(\text{Code } C \text{ is relevant \& Code } C \text{ is in problem list } P)/\text{PROB}(\text{Code } C \text{ is in problem list } P) \quad (2)$$

Assuming that all relevant codes are contained in the problem list, the numerator of Equation (2) is equal to:

$$\text{PROB(Code } C \text{ is relevant)} \quad (3)$$

Disclosed approaches for ranking codes in the PL by relevance are based on the insight that both the numerator and the denominator can be estimated by analysis of retrospective data. The probability PROB(Code C is relevant) can be estimated as (# of clinical history sections of radiology reports from which code C can be extracted)/(# of reports). This estimation leverages typical practice in which the radiologist includes in the clinical history section clinical information that is relevant for the interpretation. The probability PROB(Code C is in problem list P) is estimated as (# of problem lists containing code C)/(# of problem lists).

Various approaches are disclosed herein for estimating the above two parameters from retrospective data, and for handling codes that were not or rarely found in any clinical history and/or problem list.

Figure 1:
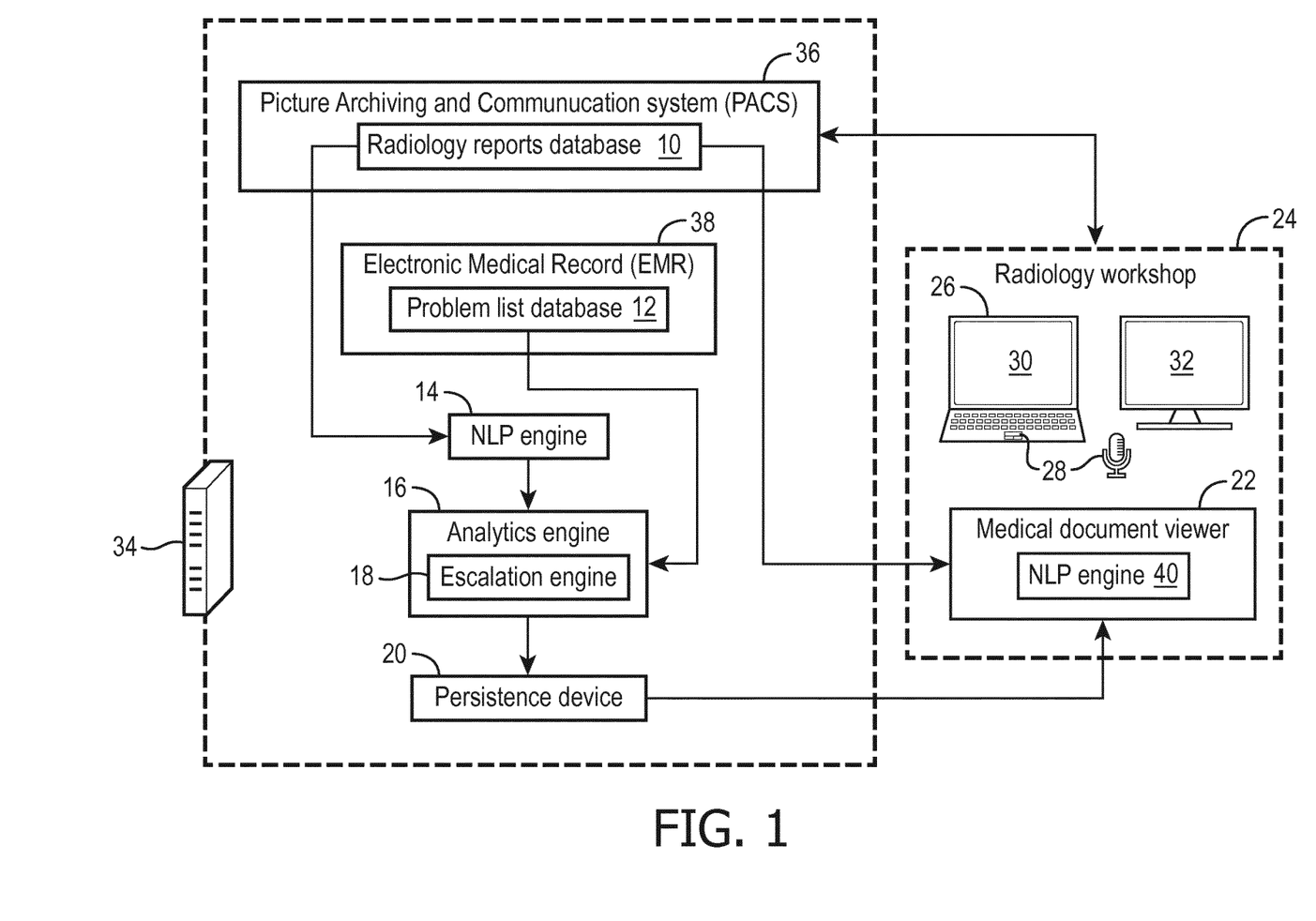
FIG. 1 diagrammatically illustrates a radiology workstation incorporating an embodiment of the disclosed clinical code contextual relevance ranking.

With reference to FIG. 1, some illustrative embodiments include the following components:

Radiology reports database 10—A database of radiology reports indexed with unique patient identifiers and contextual parameters such as the imaged anatomical section (e.g., abdomen/neuro/chest/angio/breast) and imaging modality (e.g., CR/MR/CT/NM).

Problem list (PL) database 12—A database of problem lists indexed with unique patient identifiers.

Natural language processing engine 14—A natural language processing (NLP) engine that extracts codes from particular fragments of narrative language. The codes are controlled semantical entities from a background ontology, such as ICD.

Analytics engine 16—A statistical engine that tabulates the relevant counts and aggregated them in a code-specific relevance score.

Escalation engine 18—A hierarchical reasoning engine that determines the relevance of codes based on the relevance of ancestor codes in the background ontology (e.g., "Benign Neoplasm" has "Neoplasm" among its ancestors).

Persistence device 20—A method to persist the automatically derived relevance scores and expose them to human and/or automated agents.

A medical document viewer 22 may also be provided, which serves as a viewer of medical documents that may, for example, have "heat map functionality" for contextual radiological relevance.

In illustrative FIG. 1, the clinical code contextual relevance ranking is shown in operative connection with a radiology workstation 24 that provides a radiologist or other medical professional with tools for performing and recording the reading of a radiology examination (e.g. CT, MR, PET, CR, or so forth). The illustrative radiology workstation 24 includes a computer 26 (with a microprocessor, not shown), user input devices 28 (e.g. illustrative keyboard, track pad, dictation microphone; additional or other user input devices may be provided such as a mouse and/or touch-sensitive display). The illustrative radiology workstation 24 further includes one or more (illustrative two) display devices or components 30, 32, e.g. LCD displays. Preferably at least one of these display components 30, 32 is a high resolution display for displaying medical images. The radiology workstation 24 executes suitable programming or software to enable the user to: retrieve medical images from a Picture Archiving and Communication System (PACS) 36 (also known in the art by similar nomenclatures such as a Radiology Information System, RIS); display the images on the display components 30, 32 preferably with the ability to perform various image manipulations (zooming in/out, flipping through image slices of a stack of image slices, producing three-dimensional renderings, marking locations on an image and measuring distances between markings, or so forth); prepare a text-based radiology report (e.g. by typing and/or dictation, optionally with links to medical images and/or inserted image thumbnails or reduced-resolution embedded images or so forth). The illustrative medical document viewer 22 is executed by suitable programming executing on the radiology workstation 24 to display and permit editing of such a radiology report (or, optionally more generally, to present other types of medical reports).

With continuing reference to FIG. 1, some illustrative embodiments of the components of the illustrative clinical code contextual relevance ranking are described next. These components (with the exception of the illustrative medical document viewer 22 implemented on the radiology workstation 24) are suitably implemented on a server computer 34 or other computing system (e.g. server cluster, cloud computing resource, et cetera, again each of these inherently includes one or more microprocessors) programmed by suitable software in accord with embodiments disclosed herein to perform the disclosed processing. In other embodiments, if the radiology workstation 24 has sufficient computing capacity then all components including the components of the illustrative clinical code contextual relevance ranking may be implemented locally on the radiology workstation 24. Other partitioning of the various processing amongst one, two, or more computers is also contemplated.

The radiology reports database 10 comprises a database of radiology reports, preferably stored using a standard (e.g., relational) database technology. The database can be obtained by querying an existing database for radiology reports and pertinent metadata, such as the Picture Archiving and Communication System (PACS) 36.

The problem lists database 12 comprises a database of problem lists, preferably stored using a standard (e.g., relational) database technology. The problem lists database 12 can be obtained by querying an existing database for problem lists, such as an Electronic Medical Record (EMR) 38. The patient identifiers used in the problem lists database 12 should be consistent with (e.g. the same as or capable of cross-referencing with) the identifiers used in the radiology reports database 10. This is generally the case in a typical setting such as a hospital in which patient identifiers in the EMR 38 and PACS 36 should be internally consistent.

The natural language processing (NLP) engine 14 operates to extract concepts corresponding to clinical codes (for example, ICD-10 codes) by natural language processing of radiology reports from the radiology reports database 10. In one illustrative example, this is done by: (1) detecting and normalizing section headers in radiology reports, and (2) extracting concepts from one or more fragments, such as the clinical history section. Step (1) can be implemented using sentence boundary detection based on string-matching or statistical techniques. Step (2) can be implemented using concept extraction engines, such as MetaMap, which is optimized for extracting SNOMED concepts. As an optional step, concepts extracted from another ontology other than ICD, can be mapped onto ICD using predetermined mapping tables—for example, a mapping table for SNOMED to ICD is publicly available. Thus, the NLP engine 14 detects phrases representing clinical concepts that are identified in the SNOMED concepts database and thereby indexed by SNOMED code, and the SNOMED code is then converted to an ICD-10 code using the SNOMED-to-ICD-10 mapping table. By combining information provided by Steps (1) and (2), a given one or more reports can be queried for the ICD codes residing in their clinical history section.

It should be noted that while International Statistical Classification of Diseases and Related Health Problems (ICD) codes are used herein as the clinical code ontology, more generally the approach can be used with any clinical code ontology. Similarly, while ICD-10 codes are used herein, the ICD revision may be other than the $10^{th}$ revision.

An illustrative example of implementation of the analytics engine 16 is next described. For a given ICD code C, the analytics engine 16 tabulates the following parameters, based on querying the radiology reports database 10, the problem list database 12 and the NLP engine 14:
- # of clinical history sections from which C was extracted by the natural language processing engine 14
- # of clinical history sections examined, i.e., # reports in the radiology reports database 10
- # of problem lists that contain C
- # of problem lists examined, i.e., # problem lists in problem list database 12

For an arbitrary ICD code C, the relevance is then computed using the relevance score formulas:

$$\text{PROB}(\text{Code } C \text{ is relevant}) = (\text{\# of clinical history sections of radiology reports from which code } C \text{ can be extracted})/(\text{\# of reports}) \quad (4)$$

and $$\text{PROB}(\text{Code } C \text{ is in problem list } P) = (\text{\# of problem lists containing code } C)/(\text{\# of problem lists}) \quad (5)$$

The relevance of the code C is then computed from the results of Equations (4) and (5) as:

$$\text{PROB}(\text{Code } C \text{ is relevant}|\text{Code } C \text{ is in problem list } P) = \text{PROB}(\text{Code } C \text{ is relevant})/\text{PROB}(\text{Code } C \text{ is in problem list } P) \quad (6)$$

where Equation (6) follows from the insight described with reference to Equations (1)-(3).

Using the metadata stored for each radiology report, contextual relevance scores can be computed. For instance, if it is desired to retrieve relevance scores for an abdomen study, the analytics engine 16 derives the following counts:
- # of clinical history sections from abdomen reports from which C was extracted by the NLP engine 14
- # of clinical history sections examined from abdomen reports, i.e., # abdomen reports in the radiology reports database 10
- # of problem lists of patients with a recent abdomen study (<1 yr) that contain C
- # of problem lists of patients with a recent abdomen study (<1 yr) examined, i.e., # problem lists of patients with a recent abdomen study (<1 yr) in the problem list database 12

These values then serve as inputs to Equations (4)-(6) to compute the contextual relevance score for the context of an abdomen study. In the same way additional or other, optionally more granular, contextual relevance scores can be facilitated, such as "abdomen MR" study or "chest CR read by Dr. Doe" as long as the reports of the radiology reports database 10 are appropriately indexed so that the appropriate radiology reports can be identified.

Figure 2:
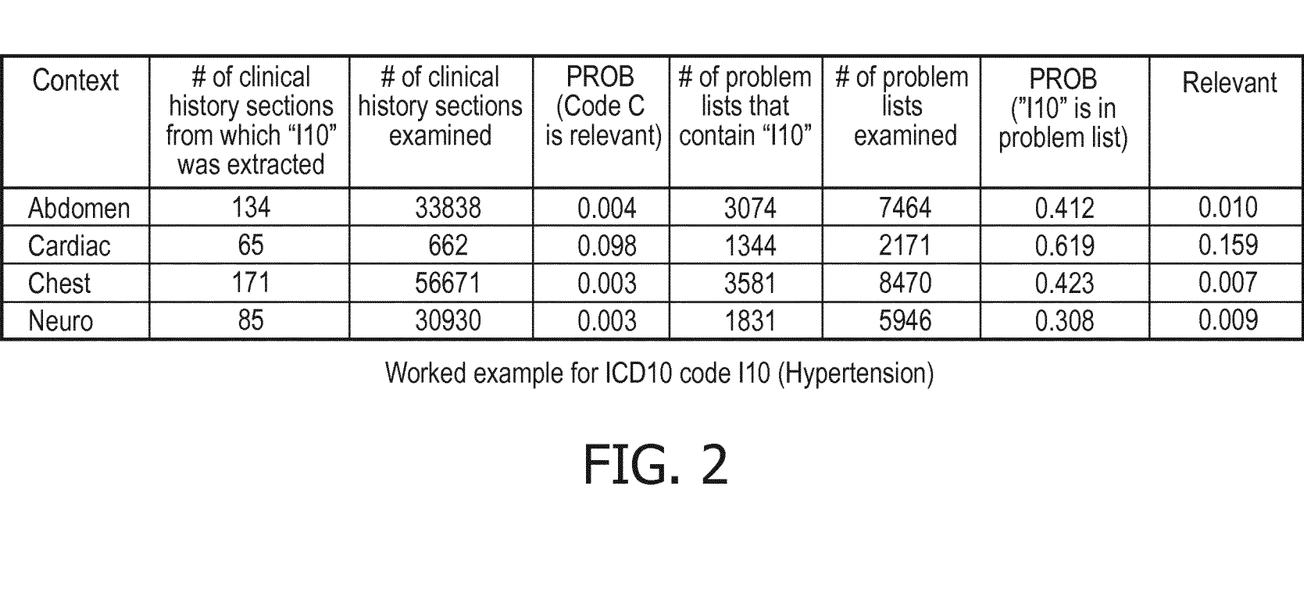
FIGS. 2-8 present experimental data as described herein.

With reference to FIG. 2, a worked example is presented for ICD10 code I10 (Hypertension). As expected the code has highest relevance score in the cardiac domain. In the example of FIG. 2, as well as those described with reference to FIGS. 3-8, the following data and analysis was employed. The code relevance metric of Equations (4)-(6) was used to rank ordered ICD10 codes that are more frequent in the history sections of radiology reports (thus assumed relevant normalized by frequency in a set of PLs). To determine code frequency, MetaMap detected code occurrences in a de-identified corpus of 243,374 reports; PLs of 20,148 patients were used for frequency normalization. The relevance metric was contextualized for neuroimaging exams by filtering for neuro reports and relevant PLs of patients with neuro exams. A similar process was used for abdomen, musculoskeletal, cardiac and chest examinations.

An illustrative embodiment of the escalation engine 18 is next described. The rationale for including this optional component is as follows. Counts aggregated by the analytics engine 16 are based on observed frequencies. For some ICD codes, these observed frequencies may be too small for meaningful analysis, in the sense that the confidence interval of the two observed probabilities, PROB(Code C is relevant) and PROB(Code C is in problem list), is too wide. For instance, consider the following parameters:
- # of problem lists that contain code C=1
- # of problem lists examined=1000
- PROB(Code C is in problem list)=0.001

In this event, the 95% confidence interval of PROB(Code C is in problem list) ranges from 0.000025 to 0.006. If PROB (Code C is relevant)=0.0005, then the confidence interval analysis indicates that the relevance scores would range from 1 (=min{0.0005/0.000025, 1}) to 0.083 (0.0005/0.006).

Figure 3:
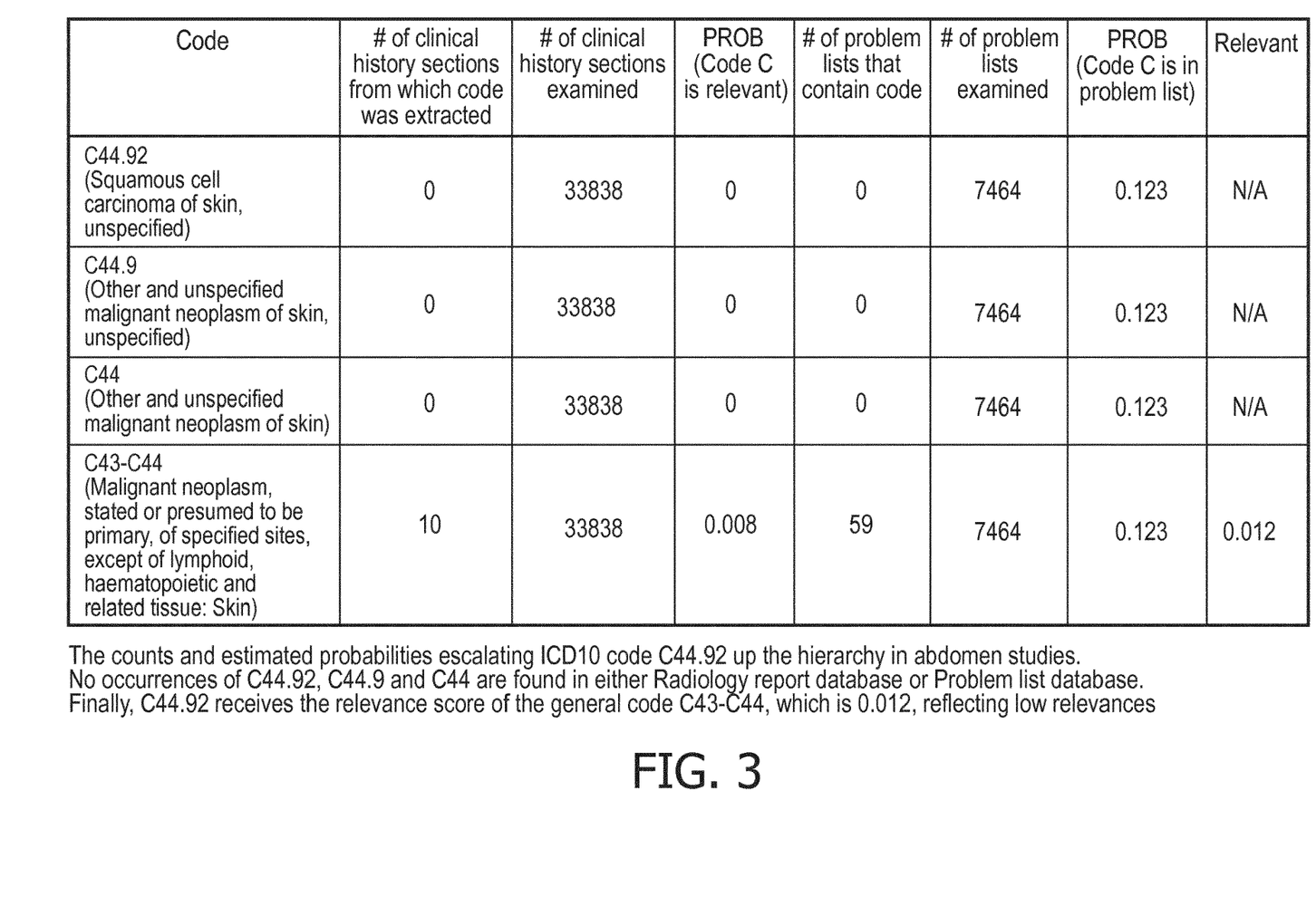

The escalation engine 18 conducts a statistical analysis for a given code and takes appropriate action if the outcome of the statistical analysis indicates that the relevance score is not trustworthy. Trustworthiness is determined is based on the type of argument given above, or, in an alternative embodiment, by checking counts against pre-determined thresholds, such as, for instance:

$$\text{\# of problem lists that contain code } C > T_{min} \quad (7)$$

where $T_{min}$ is some threshold value, e.g. $T_{min}=10$ in some contemplated embodiments. If the statistical analysis indicates that the relevance score is not trustworthy, the escalation engine 18 iteratively seeks the relevance score of a code that is more general than the current code until a trustworthy value is obtained. In this analysis, the counts of the ancestor nodes are cumulative with respect to the counts of their children and grandchildren. This will result in higher counts, higher probabilities, relatively smaller confidence intervals, and more trustworthy relevance scores. The escalation engine 18 may leverage the hierarchical tree-structures of ICD codes. This escalation strategy is illustrated in FIG. 3.

This is merely one illustrative escalation approach. Different escalation strategies can be implemented. For instance, a default relevance score can be returned for codes that do not meet the trustworthiness check, in which case there is effectively no hierarchical escalation. In other implementation, each code is always escalated up to a sufficiently general code level.

Some suitable embodiments of the persistence device 20 are next described. The persistence device 20 exposes the relevance scores to the user or to an application such as the illustrative medical document viewer 22, for example as a table file that maps individual ICD codes onto a relevance score, or as a digital object for consumption by a problem list ranking method.

Figure 4:
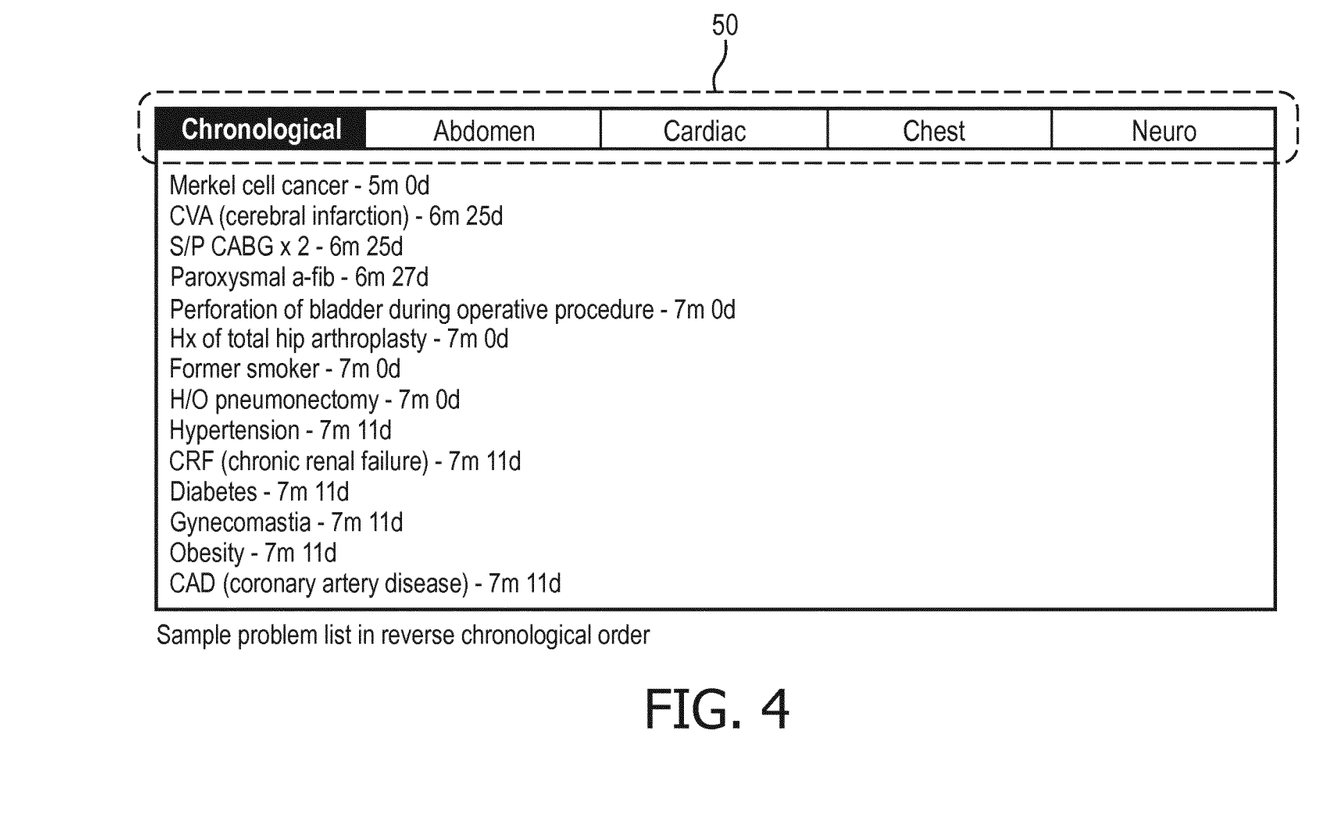
Figure 5:
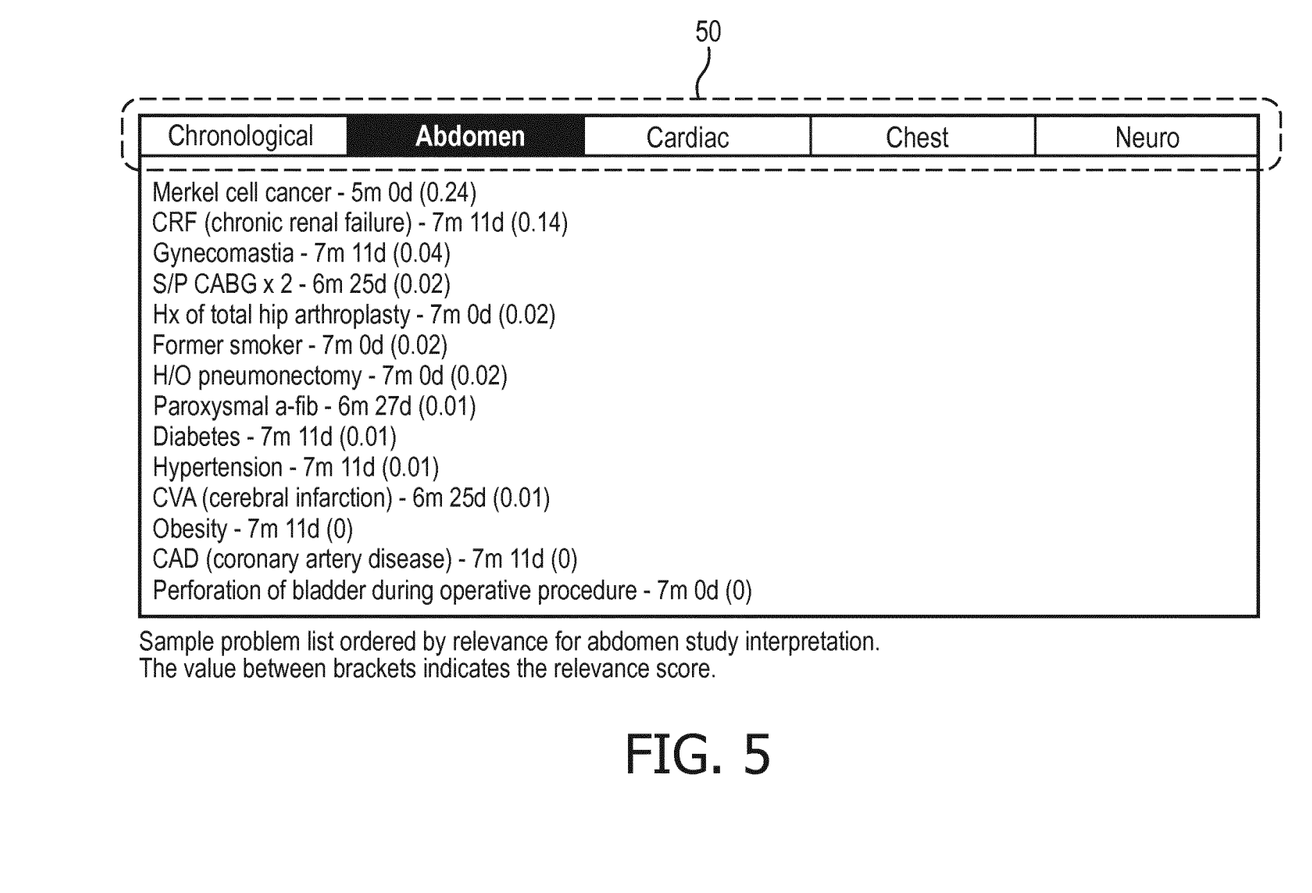
Figure 6:
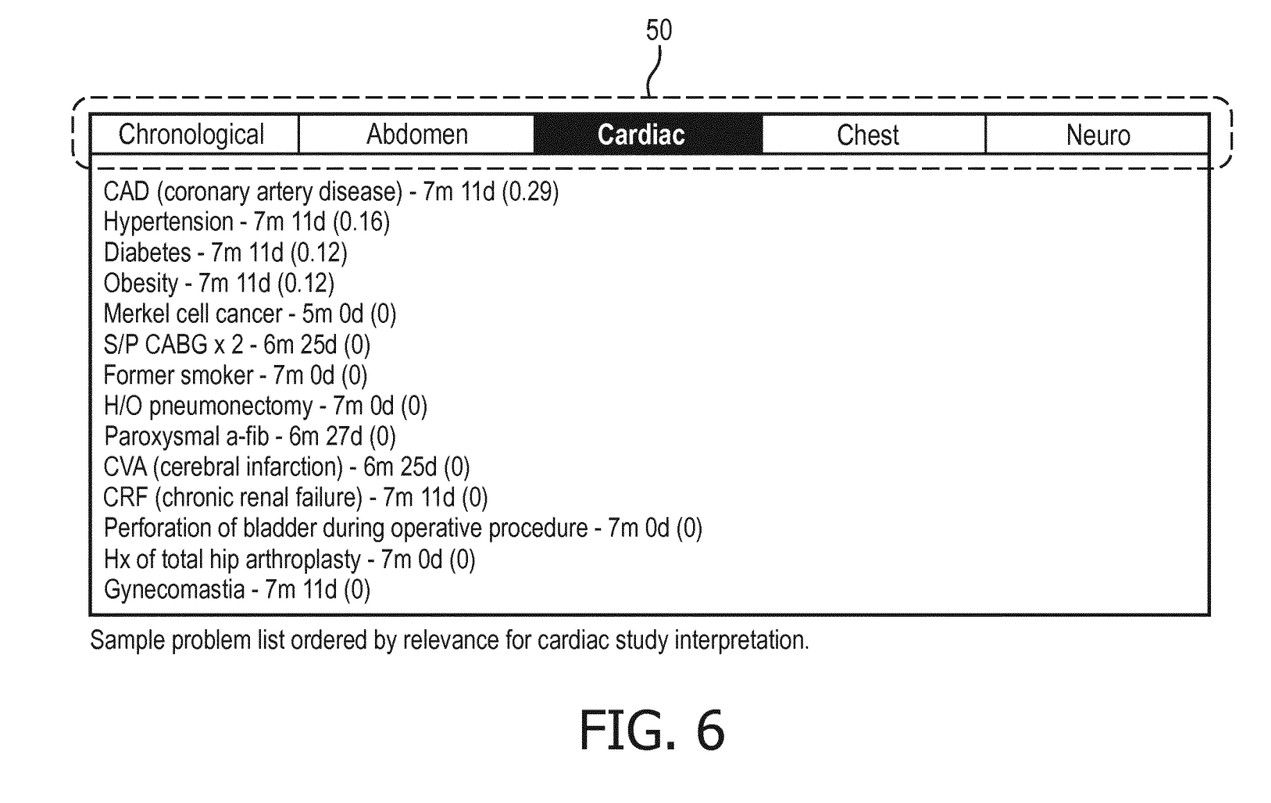
Figure 7:
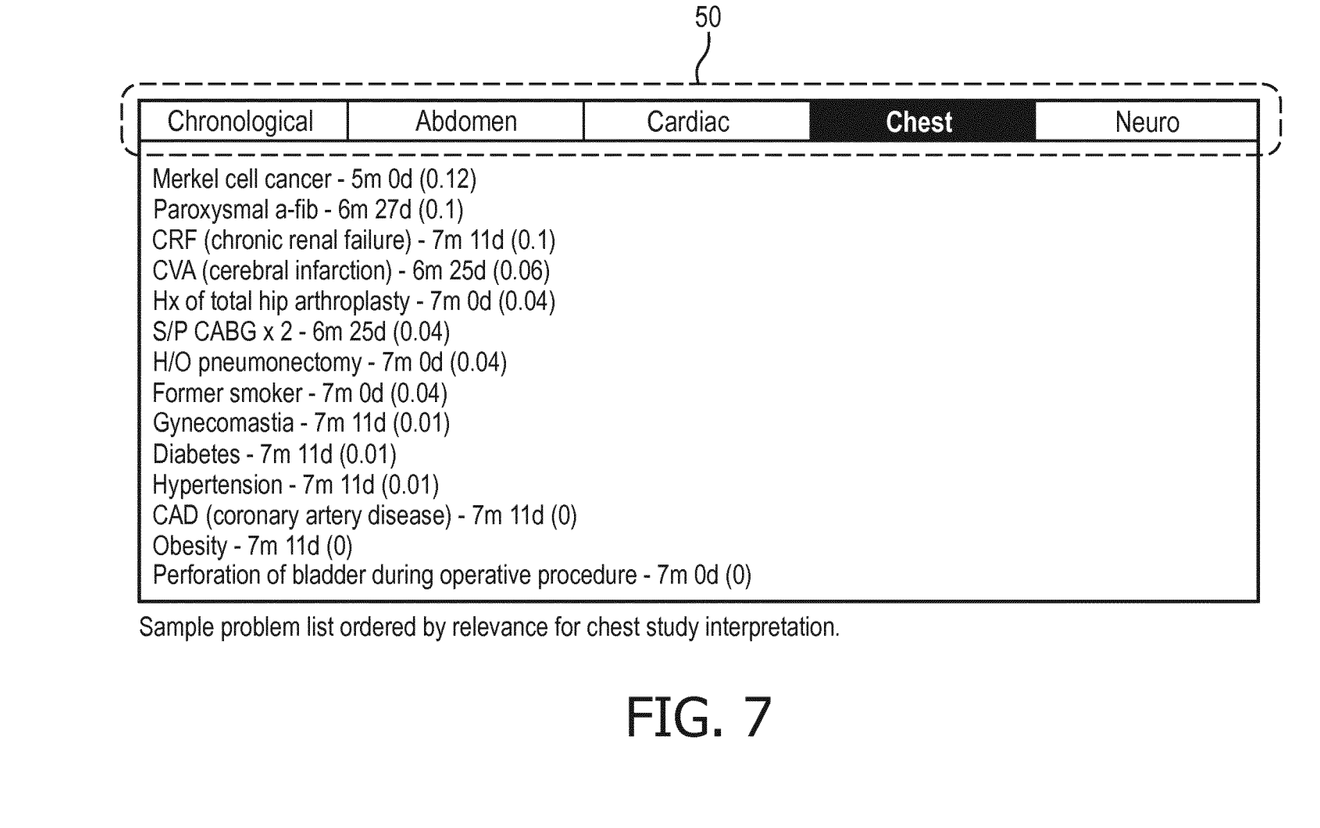
Figure 8:
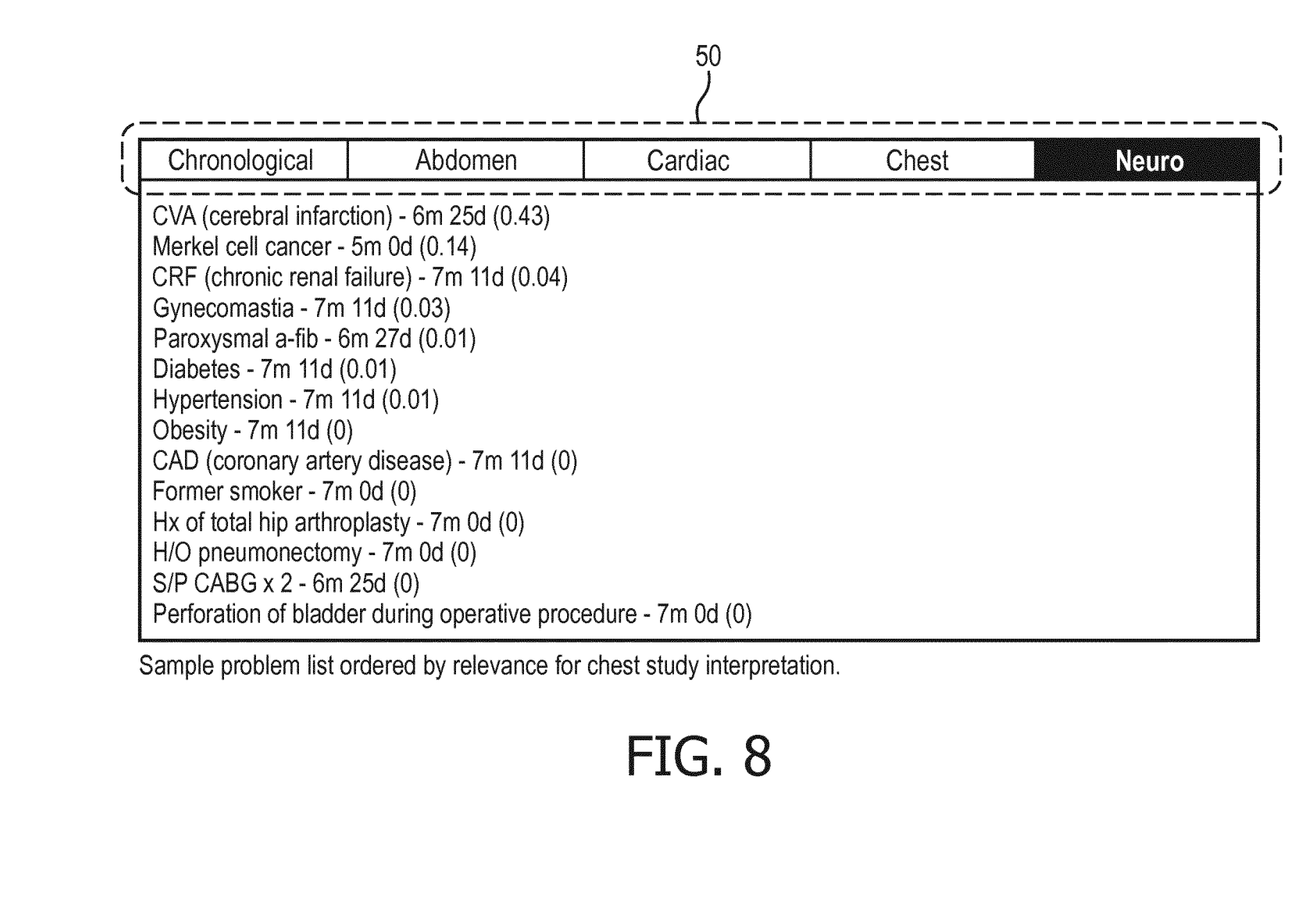

With reference to FIGS. 4-8, a further example is given. The sample problem list (PL) is shown in FIG. 4 (under the tab "Chronological"). In this table, the codes are ranked in reverse chronological order ("newest to oldest"). The contextualized rankings for abdomen, cardiac, chest and neuro are shown in FIGS. 5, 6, 7, and 8 respectively. These FIGS. 4-8 illustrate one possible user interface approach, in which one of the tables of FIGS. 4-8 are displayed on the display 30, 32 of the radiology workstation 24 (see FIG. 1) with the user being able to select from the upper graphical user interface (GUI) menu 50 any of: the "Chronological" tab to bring up the table of FIG. 4; the "Abdomen" tab to bring up the table of FIG. 5; the "Cardiac" tab to bring up the table of FIG. 6; the "Chest" tab to bring up the table of FIG. 7; or the "Neuro" tab to bring up the table of FIG. 8. In this way, the radiologist can quickly identify the most relevant ICD codes (or, in FIGS. 4-8, their equivalent clinical meanings written in natural language text) by clicking on the relevant context tab in the upper menu 50 using the illustrative track pad or some other pointing device 28 (e.g. mouse, trackball, touch-sensitive screen).

In a contemplated variant embodiment, the radiology reports database 10 and the problem list database 12 are configured such that for each radiology report in the former database an image of the then-current problem list is preserved. In this manner, it would be possible to obtain the patient's problem list for each time point of radiological interpretation. When configured in this manner, the clinical codes ranking can be applied as already described using the time history-appropriate problem list.

In another contemplated variant, the "latency" of an ICD code is taken into account, defined as the duration of the interval spanned by the time point the code was entered and the time point of radiological interpretation (or "now"). Each ICD code extracted from the clinical history section of a report, can be matched against the then-current problem list and the code's latency can be obtained. For each code, a time dependence curve can be created indicating how the relevance of a code deteriorates over time. In this manner, it can be established that fever is relevant if reported within two years, but not more than that. Similarly, it can be establishes that the relevance curve of malignant neoplasms is stable, indicating that its relevance is not impacted by time.

Some further approaches for leveraging the clinical code rankings in the context of a radiology workstation 24 are next described.

When the medical document viewer 22 is launched to open a new radiology examination of a patient, the viewer 22 retrieves the one or more medical documents from one or more medical repositories (e.g. the EMR 38 or PACS 36) and applies an NLP engine 40 to them to extract sentences and extract ICD codes. For each concept a relevance score is calculated as already described. Sentences or phrases from which codes were extracted with high relevance can be highlighted in the report displayed on the display component 30, 32 of the radiology workstation 24, or can be presented separately. On the other hand, a sentence from which codes were extracted with only low relevance scores may be shown in a grayed-out or otherwise de-emphasized format, or may be presented using ellipses (" . . . ") as placeholders with the "hidden" text being optionally selected for display by the user clicking on (or hovering over, or otherwise selecting) the ellipsis using a pointing device. The medical document viewer 22 can further be configured to only highlight/separate sentences from a select set of sections (e.g., impression and clinical history). These are merely illustrative examples.

It will be further appreciated that the disclosed processing may optionally be implemented as a non-transitory storage medium storing instructions (e.g. a computer program) that is readable and executable by a computer (e.g. the illustrative server 34 and/or the computer 26 of the radiology workstation 24 of FIG. 1) to perform the disclosed clinical code relevance ranking and presentation operations. The non-transitory storage medium may, for example, comprise a hard disk or other magnetic storage medium, an optical disk or other optical storage medium, a solid state disk drive or other electronic storage medium, various combinations thereof, or so forth.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A radiology workstation comprising:
first and second display components;
at least one user input device; and
at least one microprocessor programmed to:
during a reading of a radiology examination:
receive a selection of the radiology examination via the at least one user input device and retrieving the radiology examination;
display and manipulate the medical images of the radiology examination on the first display component of the radiology workstation; and
receive via the at least one user input device and displaying, on the second display component, a text-based radiology report for the radiology examination; and
during the reading of the radiology examination, generate a contextual ranking of clinical codes for a context comprising the radiology examination selected via the at least one user input device and display information pertaining to the contextual ranking as a ranked list or table on the second display component of the radiology workstation;
wherein the contextual ranking is computed by the microprocessor from: (i) statistics of the clinical codes in problem lists contained in a problem lists database and satisfying the context; and
(ii) statistics of occurrences of the clinical codes in radiology reports contained in a radiology reports database, the statistics of occurrences including at least a number of clinical history sections of radiology reports satisfying the context from which the clinical code is extracted by:
determining a number of counts of the statistics of occurrences of the clinical codes; and
conducting a statistical analysis of the determined number of counts; and
calculating a trustworthiness of the determined number of counts based on the conducted statistical analysis.

2. The radiology workstation of claim 1 wherein the context includes an anatomical section and an imaging modality.

3. The radiology workstation of claim 1 wherein the contextual ranking of a clinical code is computed from statistics of occurrences of the clinical codes in radiology reports contained in a radiology reports database including at least:

a number of clinical history sections of radiology reports satisfying the context from which the clinical code is extracted;

a total number of reports satisfying the context;

a number of problem lists satisfying the context that contain the clinical code; and a total number of problem lists satisfying the context.

4. The radiology workstation of claim 1 wherein the microprocessor is programmed to generate the statistics of occurrences of the clinical codes in radiology reports by extracting the clinical code from radiology reports by performing natural language processing to identify phrases representing one or more clinical concepts corresponding to the clinical code.

5. The radiology workstation of claim 1 wherein the clinical codes are International Statistical Classification of Diseases and Related Health Problems (ICD) codes.

6. The radiology workstation of claim 1 wherein the microprocessor is programmed to display information pertaining to the contextual ranking on the second display component by:

displaying a medical report satisfying the context on the second display component; and on the second display component, highlighting sentences or phrases of the medical report from which clinical codes with high relevance were extracted.

7. A non-transitory computer readable medium storing instructions executable by at least one processor to perform an image acquisition method, the method including:

displaying medical images on a first display component of a radiology workstation;

generating a contextual ranking of International Statistical Classification of Diseases and Related Health Problems (ICD) codes for a context received via at least one user input device of the radiology workstation; and displaying information pertaining to the contextual ranking on a second display component of the radiology workstation;

wherein the contextual ranking is generated from (i) statistics of occurrences of the ICD codes in radiology reports contained in a radiology reports database including at least a number of clinical history sections of radiology reports satisfying the context from which the clinical code is extracted and (ii) statistics of the ICD codes in problem lists contained in a problem lists database and satisfying the context;

wherein the contextual ranking is further computed by the microprocessor from (i) the statistics of occurrences of the clinical codes in the radiology reports contained in the radiology reports database including at least a number of clinical history sections of radiology reports satisfying the context from which the clinical code is extracted by:

conducting a first statistical analysis of a number of counts of the statistics of occurrences of the clinical codes; and obtaining additional counts and performing a second statistical analysis when results of the first statistical analysis does not satisfy a predetermined trustworthiness metric.

8. The non-transitory computer readable medium of claim 7, further including:

receiving the context by receiving a selection of a radiology examination via the at least one user input device wherein the context is a context of the selected radiology examination.

9. The non-transitory computer readable medium of claim 7, wherein the context includes at least one of an anatomical section and an imaging modality.

10. The non-transitory computer readable medium of claim 7, further including:

generating the contextual ranking of an ICD code C from statistics of occurrences of the ICD codes in radiology reports contained in a radiology reports database including at least:

a number of clinical history sections of radiology reports satisfying the context from which the ICD code C is extracted;

a total number of reports satisfying the context;

a number of problem lists satisfying the context that contain the ICD code C; and a total number of problem lists satisfying the context.

11. The non-transitory computer readable medium of claim 7, further including:

generating the statistics of occurrences of the ICD codes in radiology reports by extracting the ICD code from radiology reports by performing natural language processing to identify phrases representing one or more clinical concepts corresponding to the ICD code.

12. The non-transitory computer readable medium of claim 7, further including:

displaying the contextual ranking as a ranked list or table on the second display component.

13. The non-transitory computer readable medium of claim 7, further including:

displaying information pertaining to the contextual ranking on the second display component by:

displaying a medical report satisfying the context on the second display component; and on the second display component, highlighting sentences or phrases of the medical report from which ICD codes with high relevance were extracted.

14. A radiology workstation, comprising:

first and second display components;

at least one user input device; and at least one microprocessor programmed to:

control the first display component to display medical images;

generate a contextual ranking of clinical codes for a context received via the at least one user input device and display information pertaining to the contextual ranking on the second display component of the radiology workstation; and generate statistics of occurrences of the clinical codes in radiology reports contained in a radiology reports database by extracting a clinical code from radiology reports by performing natural language processing to identify phrases representing one or more clinical concepts corresponding to the clinical code;

wherein the contextual ranking is computed by the microprocessor by computing relevance of clinical code C defined as a conditional probability PROB (Code C is relevant|Code C is in problem list P) utilizing the statistics of occurrences and a problem lists database containing problem lists, the relevance of clinical code C being computed by computing:

PROB (Code $C$ is relevant)=(number of clinical history sections of radiology reports from which code $C$ is extracted)/(number of radiology reports);

PROB (Code $C$ is in problem list $P$)=(number of problem lists containing code $C$)/(number problem lists); and Relevance of clinical code $C$=PROB (Code $C$ is relevant)/PROB (Code $C$ is in problem list $P$)

15. The radiology workstation of claim 14, wherein the context is received by receiving a selection of a radiology examination via the at least one user input device wherein the context is a context of the selected radiology examination.

16. The radiology workstation of claim 14, wherein the microprocessor is programmed to display information pertaining to the contextual ranking on the second display component by:
displaying a medical report satisfying the context on the second display component; and
on the second display component, highlighting sentences or phrases of the medical report from which clinical codes with high relevance were extracted.

17. The radiology workstation of claim 14, wherein the clinical codes are International Statistical Classification of Diseases and Related Health Problems (ICD) codes.

* * * * *